United States Patent
Erb et al.

(12)

(10) Patent No.: US 6,364,876 B1
(45) Date of Patent: Apr. 2, 2002

(54) VACUUM-ASSISTED SECURING APPARATUS FOR A MICROWAVE ABLATION INSTRUMENT

(75) Inventors: Lyndall Erb, Montaro; Dany Berube, Fremont, both of CA (US); Robert Matheny, Carmel, IN (US); Robert E. Woodard; Theodore C. Ormsby, both of Hayward, CA (US)

(73) Assignee: AFx, Inc., Fremont, CA (US)

( * ) Notice: Subject to any disclaimer, the term of this patent is extended or adjusted under 35 U.S.C. 154(b) by 0 days.

(21) Appl. No.: 09/398,723

(22) Filed: Sep. 20, 1999

Related U.S. Application Data

(63) Continuation-in-part of application No. 09/178,066, filed on Oct. 23, 1998.

(51) Int. Cl.$^7$ .............................................. A61B 18/18
(52) U.S. Cl. .......................... 606/33; 606/41; 607/101; 607/156; 600/387
(58) Field of Search .................. 604/35, 176; 600/387; 607/149, 154, 155, 156, 101, 122; 606/33, 34, 41, 46

(56) References Cited

U.S. PATENT DOCUMENTS

| | | |
|---|---|---|
| 4,204,549 A | 5/1980 | Paglione |
| 4,601,296 A | 7/1986 | Yerushalmi |
| 4,641,649 A | 2/1987 | Walinsky et al. |
| 4,643,186 A | 2/1987 | Rosen et al. |
| 4,823,812 A | 4/1989 | Eshel et al. |
| 5,129,396 A | 7/1992 | Rosen et al. |
| 5,246,438 A | 9/1993 | Langberg |
| 5,314,466 A | 5/1994 | Stern et al. |
| 5,344,441 A | 9/1994 | Gronauer |
| 5,370,644 A | 12/1994 | Langberg |
| 5,405,346 A | 4/1995 | Grundy et al. |
| 5,800,494 A | 9/1998 | Campbell et al. |
| 5,861,021 A | 1/1999 | Thome et al. |
| 5,971,983 A | * 10/1999 | Lesh ............................ 606/41 |
| 6,004,269 A | * 12/1999 | Crowley et al. ............. 600/439 |
| 6,027,497 A | * 2/2000 | Daniel et al. ................. 606/15 |
| 6,086,583 A | * 7/2000 | Ouchi .......................... 606/41 |
| 6,161,543 A | * 12/2000 | Cox et al. .................... 128/898 |
| 6,171,303 B1 | * 1/2001 | Ben-Haim et al. ............ 606/15 |

FOREIGN PATENT DOCUMENTS

| | | |
|---|---|---|
| EP | 0048402 A1 | 3/1982 |
| EP | 0139607 A1 | 5/1985 |
| EP | 0248758 A1 | 12/1987 |
| WO | WO94/02204 | 2/1994 |

OTHER PUBLICATIONS

C. H. Durney and M. F. Iskander, "Antennas for Medical Applications", Chapter 24, pp. 24–2, 24–27, 24–28, 24–29, and 24–58.

\* cited by examiner

*Primary Examiner*—Linda C. M. Dvorak
*Assistant Examiner*—David M. Ruddy
(74) *Attorney, Agent, or Firm*—Beyer Weaver & Thomas

(57) ABSTRACT

A securing apparatus for selectively securing an ablating element of an ablation instrument proximate to a targeted region of a biological tissue. The securing apparatus includes a support base affixed to the ablation instrument relative the ablating element, and having a support face adapted to seat against the biological tissue proximate to the ablation element. The support base further defines a passage having one end communicably coupled to a vacuum source and an opposite end terminating at an orifice at the support face. The support face together with the biological tissue forms a hermetic seal thereagainst during operation of the vacuum source to secure the ablation instrument thereagainst. Essentially, the hermetic seal and the vacuum source cooperate to form a vacuum force sufficient to retain the ablation device against the biological tissue.

24 Claims, 10 Drawing Sheets

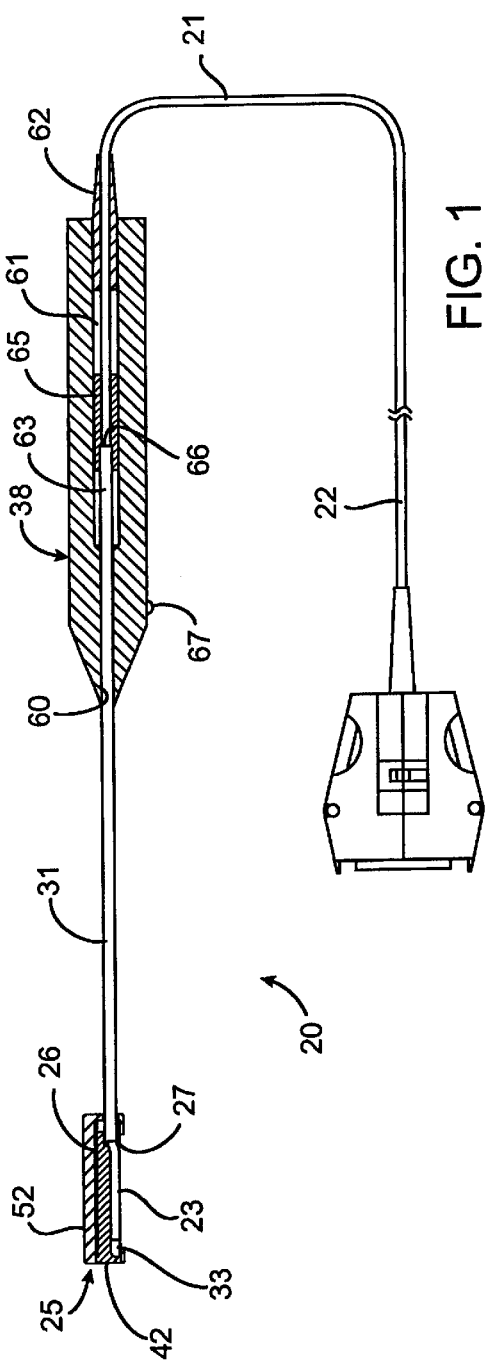
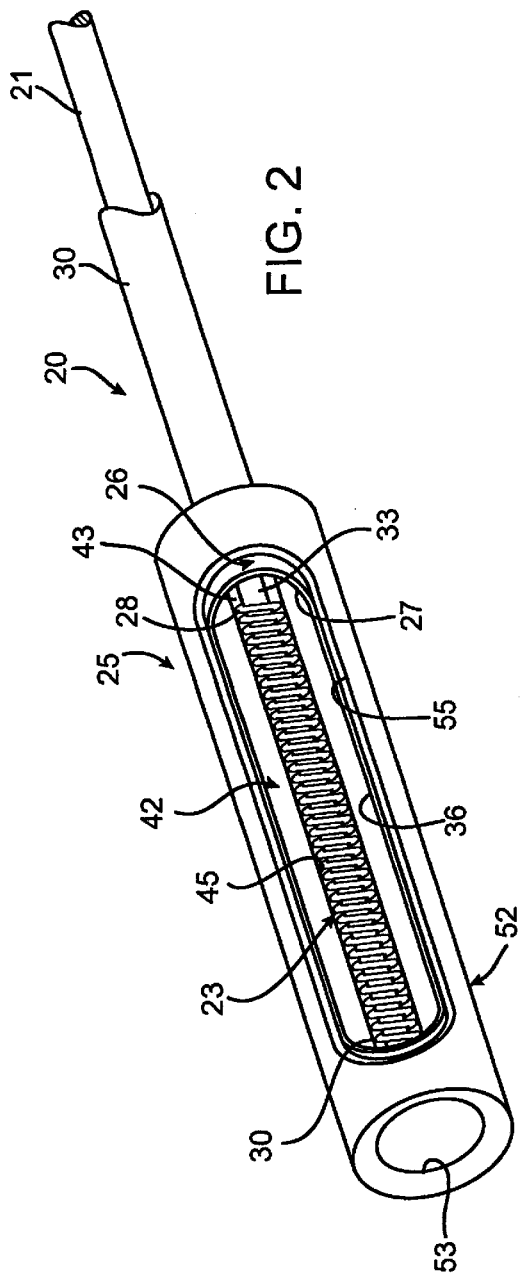
FIG. 1
FIG. 2

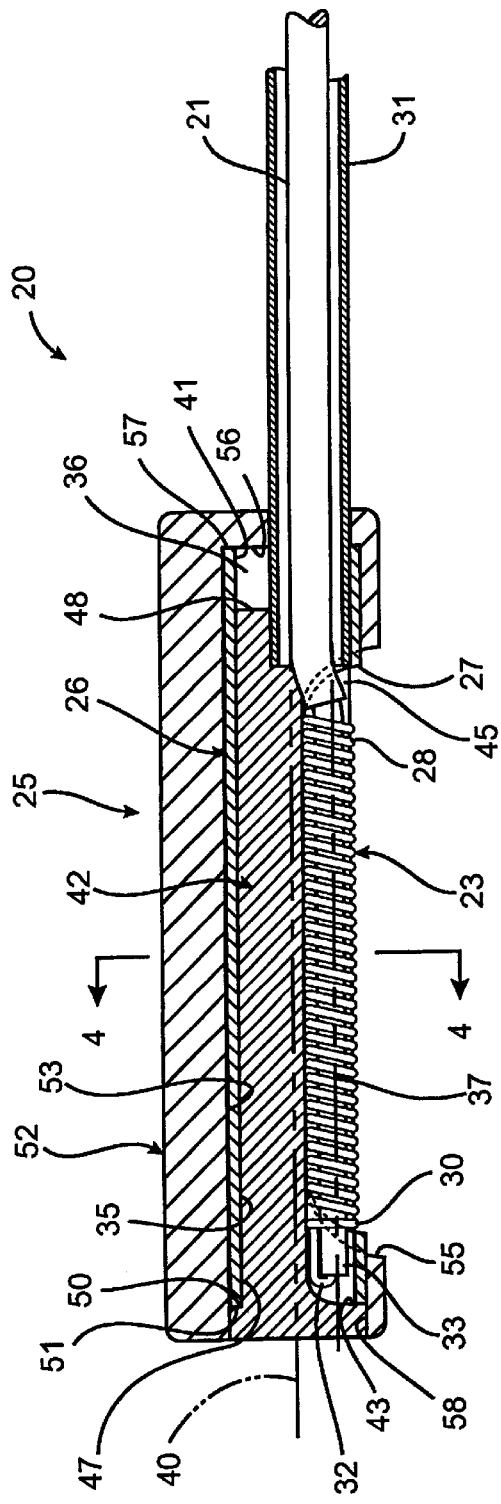
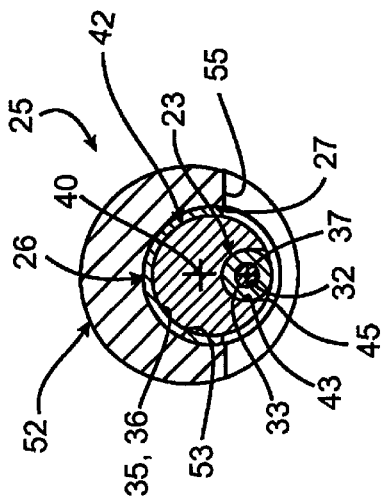
FIG. 3
FIG. 4

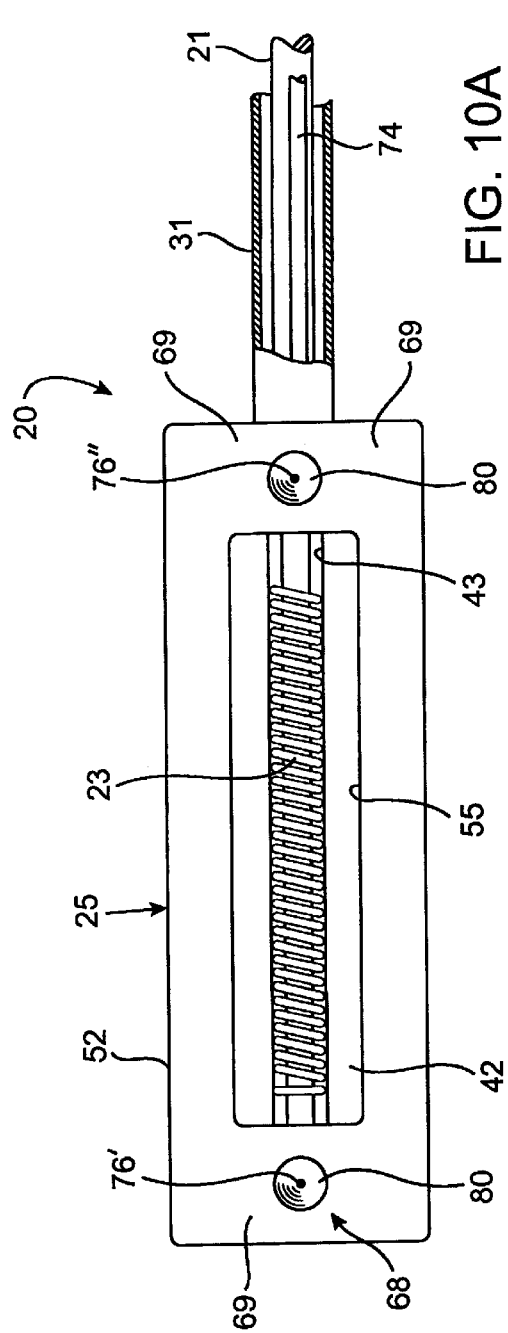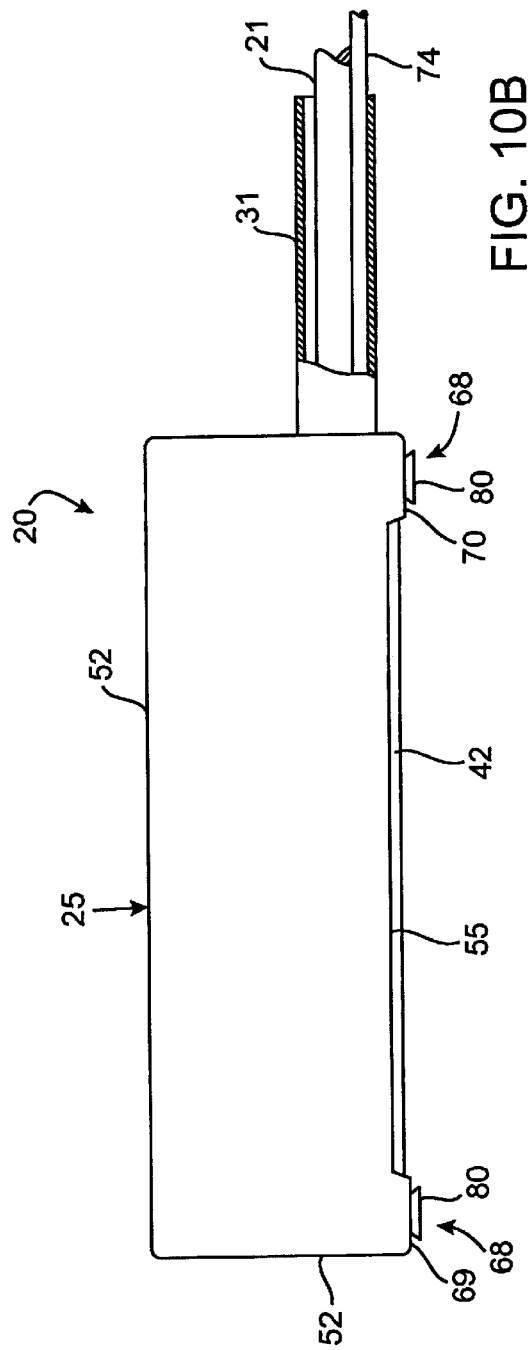

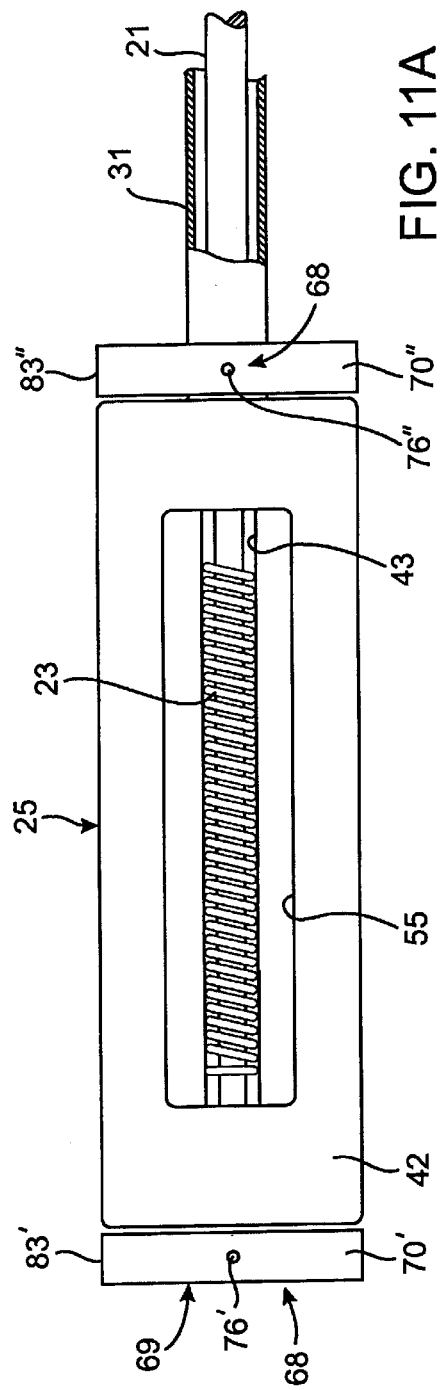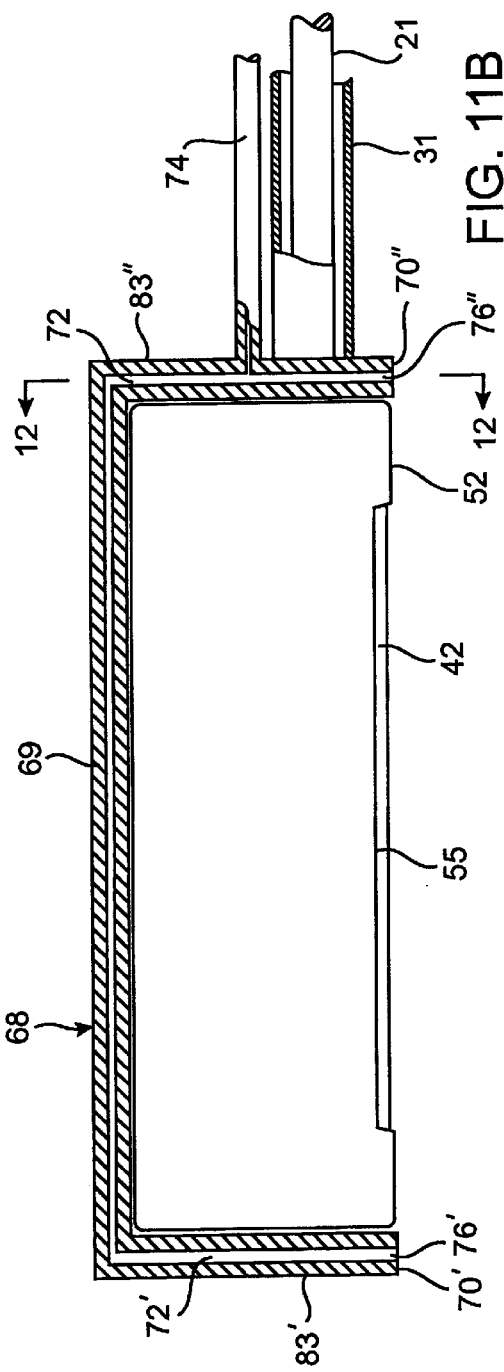

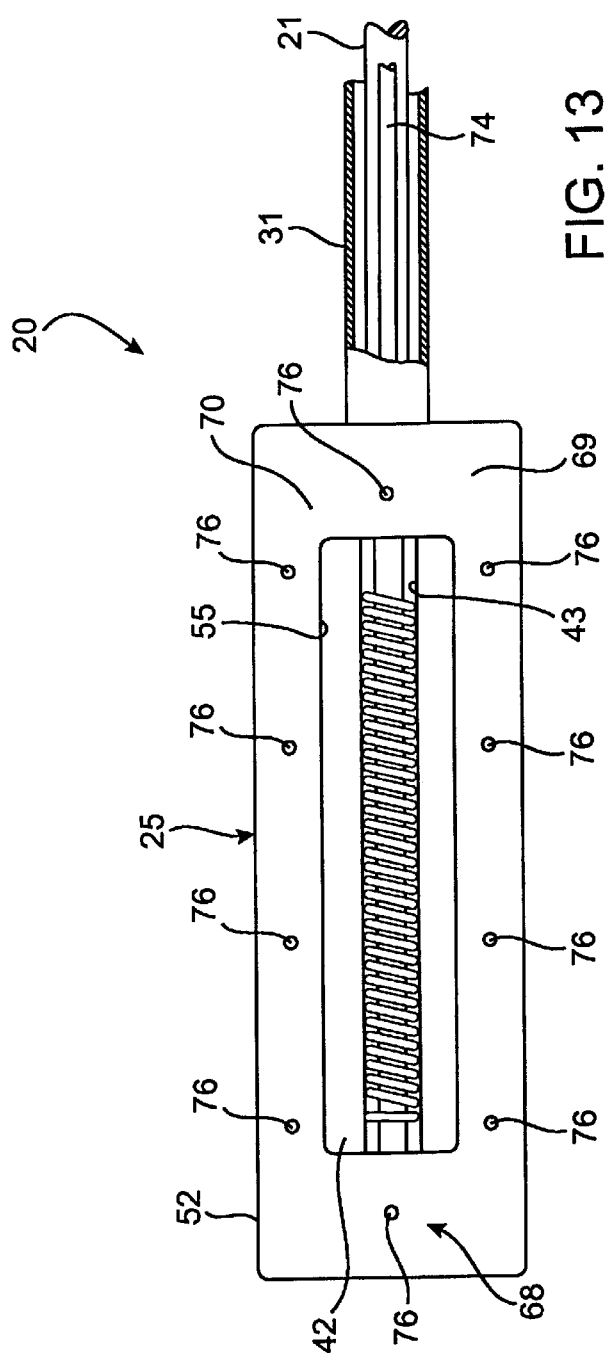
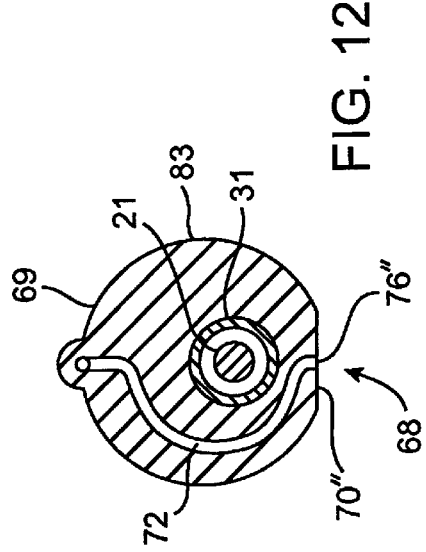
FIG. 13
FIG. 12

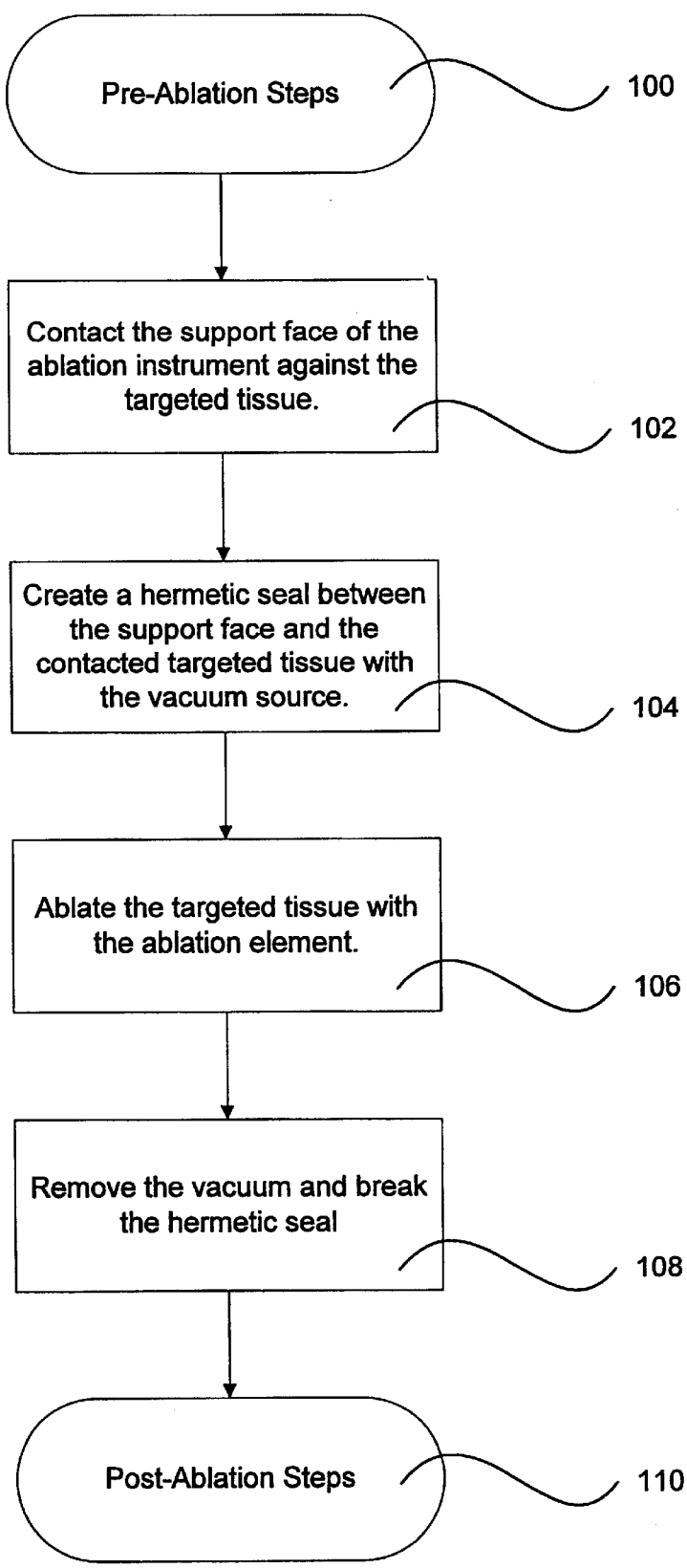
FIG._14

VACUUM-ASSISTED SECURING APPARATUS FOR A MICROWAVE ABLATION INSTRUMENT

CROSS REFERENCE TO RELATED APPLICATION

This is a Continuation-in-part application of co-pending prior application Ser. No. 09/178,066 filed on Oct. 23, 1998, the disclosure of which is incorporated herein by reference.

The present application is a Continuation-In-Part of U.S. patent application Ser. No. 09/178,066, filed Oct. 23, 1998, and entitled, "Directional Reflector Shield assembly For a Microwave Ablation Instrument", which is incorporated herein by reference in its entirety for all purposes.

BACKGROUND OF THE INVENTION

1. Field of Invention

The present invention relates, generally, to ablation instrument systems that use electromagnetic energy in the microwave frequencies to ablate internal bodily tissues, and, more particularly, to antenna arrangements and instrument construction techniques that direct the microwave energy in selected directions that are relatively closely contained along the antenna.

2. Description of the Prior Art

It is well documented that atrial fibrillation, either alone or as a consequence of other cardiac disease, continues to persist as the most common cardiac arrhythmia. According to recent estimates, more than two million people in the U.S. suffer from this common arrhythmia, roughly 0.15% to 1.0% of the population. Moreover, the prevalence of this cardiac disease increases with age, affecting nearly 8% to 17% of those over 60 years of age.

Although atrial fibrillation may occur alone, this arrhythmia often associates with numerous cardiovascular conditions, including congestive heart failure, mitral regurgitation, hypertensive cardiovascular disease, myocardial infarction, rheumatic heart disease, and stroke. Regardless, three separate detrimental sequelae result: (1) a change in the ventricular response, including the onset of an irregular ventricular rhythm and an increase in ventricular rate; (2) detrimental hemodynamic consequences resulting from loss of atroventricular synchrony, decreased ventricular filling time, and possible atrioventricular valve regurgitation; and (3) an increased likelihood of sustaining a thromboembolic event because of loss of effective contraction and atrial stasis of blood in the left atrium.

Atrial arrhythmia may be treated using several methods. Pharmacological treatment of atrial fibrillation, for example, is initially the preferred approach, first to maintain normal sinus rhythm, or secondly to decrease the ventricular response rate. While these medications may reduce the risk of thrombus collecting in the atrial appendages if the atrial fibrillation can be converted to sinus rhythm, this form of treatment is not always effective. Patients with continued atrial fibrillation and only ventricular rate control continue to suffer from irregular heartbeats and from the effects of impaired hemodynamics due to the lack of normal sequential atrioventricular contractions, as well as continue to face a significant risk of thromboembolism.

Other forms of treatment include chemical cardioversion to normal sinus rhythm, electrical cardioversion, and RF catheter ablation of selected areas determined by mapping. In the more recent past, other surgical procedures have been developed for atrial fibrillation, including left atrial isolation, transvenous catheter or cryosurgical ablation of His bundle, and the Corridor procedure, which have effectively eliminated irregular ventricular rhythm. However, these procedures have for the most part failed to restore normal cardiac hemodynamics, or alleviate the patient's vulnerability to thromboembolism because the atria are allowed to continue to fibrillate. Accordingly, a more effective surgical treatment was required to cure medically refractory atrial fibrillation of the heart.

On the basis of electrophysiologic mapping of the atria and identification of macroreentrant circuits, a surgical approach was developed which effectively creates an electrical maze in the atrium (i.e., the MAZE procedure) and precludes the ability of the atria to fibrillate. Briefly, in the procedure commonly referred to as the MAZE III procedure, strategic atrial incisions are performed to prevent atrial reentry and allow sinus impulses to activate the entire atrial myocardium, thereby preserving atrial transport function postoperatively. Since atrial fibrillation is characterized by the presence of multiple macroreentrant circuits that are fleeting in nature and can occur anywhere in the atria, it is prudent to interrupt all of the potential pathways for atrial macroreentrant circuits. These circuits, incidentally, have been identified by intraoperative mapping both experimentally and clinically in patients.

Generally, this procedure includes the excision of both atrial appendages, and the electrical isolation of the pulmonary veins. Further, strategically placed atrial incisions not only interrupt the conduction routes of the common reentrant circuits, but they also direct the sinus impulse from the sinoatrial node to the atrioventricular node along a specified route. In essence, the entire atrial myocardium, with the exception of the atrial appendages and the pulmonary veins, is electrically activated by providing for multiple blind alleys off the main conduction route between the sinoatrial node to the atrioventricular node. Atrial transport function is thus preserved postoperatively as generally set forth in the series of articles: Cox, Schuessler, Boineau, Canavan, Cain, Lindsay, Stone, Smith, Corr, Change, and D'Agostino, Jr., *The Surgical Treatment Atrial Fibrillation* (pts. 1–4), 101 THORAC CARDIOVASC SURG., 402–426, 569–592 (1991).

While this MAZE III procedure has proven effective in ablating medically refractory atrial fibrillation and associated detrimental sequelae, this operational procedure is traumatic to the patient since substantial incisions are introduced into the interior chambers of the heart. Consequently, other techniques have thus been developed to interrupt and redirect the conduction routes without requiring substantial atrial incisions. One such technique is strategic ablation of the atrial tissues through ablation catheters.

Most approved ablation catheter systems now utilize radio frequency (RF) energy as the ablating energy source. Accordingly, a variety of RF based catheters and power supplies are currently available to electrophysiologists. However, radio frequency energy has several limitations including the rapid dissipation of energy in surface tissues resulting in shallow "burns" and failure to access deeper arrhythmic tissues. Another limitation of RF ablation catheters is the risk of clot formation on the energy emitting electrodes. Such clots have an associated danger of causing potentially lethal strokes in the event that a clot is dislodged from the catheter.

As such, catheters which utilize electromagnetic energy in the microwave frequency range as the ablation energy source are currently being developed. Microwave frequency energy has long been recognized as an effective energy source for heating biological tissues and has seen use in such hyperthermia applications as cancer treatment and preheating of blood prior to infusions. Accordingly, in view of the drawbacks of the traditional catheter ablation techniques, there has recently been a great deal of interest in using microwave energy as an ablation energy source. The advantage of microwave energy is that it is much easier to control and safer than direct current applications and it is capable of generating substantially larger lesions than RF catheters, which greatly simplifies the actual ablation procedures. Typical of such microwave ablation systems are described in the U.S. Pat. Nos. 4,641,649 to Walinsky; 5,246,438 to Langberg; 5,405,346 to Grundy, et al.; and 5,314,466 to Stern, et al, each of which is incorporated herein by reference.

Most of the existing microwave ablation catheters contemplate the use of longitudinally extending helical antenna coils that direct the electromagnetic energy in a radial direction that is generally perpendicular to the longitudinal axis of the catheter although the fields created are not well constrained to the antenna itself. Although such catheter designs work well for a number of applications, such radial output, while controlled, is inappropriate for use in MAZE III procedures for example which require very strategically positioned and formed lesions. Thus, it would be desirable to provide microwave ablation catheter designs that are capable of effectively transmitting electromagnetic energy that more closely approximates the length of the antenna, and in a specific direction, such as generally perpendicular to the longitudinal axis of the catheter but constrained to a selected radial region of the antenna.

SUMMARY OF THE INVENTION

The present invention provides a securing apparatus for selectively securing an ablating element of an ablation instrument proximate to a targeted region of a biological tissue. The securing apparatus includes a support base affixed to the ablation instrument relative the ablating element, and having a support face adapted to seat against the biological tissue proximate to the ablation element. The support base further defines a passage having one end communicably coupled to a vacuum source and an opposite end terminating at an orifice at the support face. The support face together with the biological tissue forms a hermetic seal thereagainst during operation of the vacuum source to secure the ablation instrument thereagainst. Essentially, the hermetic seal and the vacuum source cooperate to form a vacuum force sufficient to retain the ablation device against the biological tissue.

In one embodiment, the support face is deformable to substantially conform to the shape of the biological tissue. One such deformable support face would be in the form of a suction cup. In another form, the orifice is provided by a proximal orifice positioned on a proximal end of the window portion, and a distal orifice positioned on a distal end of the window portion. The orifices may also be provided by a plurality of orifices spaced apart peripherally about the window portion In another aspect of the present invention, a securing apparatus is provided for selectively securing an ablating element of an ablation instrument proximate to a targeted region of a biological tissue. The securing apparatus includes a support base coupled to the ablation instrument, and which defines a passage terminating at an orifice positioned to receive the biological tissue during ablation of the ablating element. A vacuum line is in fluid communication with the support member passage; and a vacuum source is operatively coupled to the vacuum line. Upon the generation of a vacuum force by the vacuum source, sufficient to hermetically seal the support member against the biological tissue, the ablation instrument will be secured thereto.

In still another embodiment, a microwave ablation instrument for ablating biological tissue is provided including a transmission line having a proximal portion suitable for connection to an electromagnetic energy source, and an antenna coupled to the transmission line for generating an electric field sufficiently strong to cause tissue ablation. A shield assembly is coupled to the antenna to substantially shield a surrounding area of the antenna from the electric field radially generated therefrom while permitting a majority of the field to be directed generally in a predetermined direction. The shield assembly includes a support base having a support face adapted to seat against the biological tissue proximate to the antenna. A passage is defined by the support base having one end coupled to a vacuum source and an opposite end terminating at an orifice at the support face; wherein the support face forms a hermetic seal against the biological tissue during operation of the vacuum source to secure the ablation instrument thereto.

Preferably, the transmission line is suitable for transmission of microwave energy at frequencies in the range of approximately 800 to 6000 megahertz. This electric field should be sufficiently strong to cause tissue ablation in a radial direction.

In another aspect of the present invention, a method is provided for securing an ablation element of an ablation instrument to a biological tissue to be ablated. The method includes introducing the ablation instrument into a patient's body to position the ablating element of the ablation instrument adjacent to the biological tissue to be ablated; and contacting a support face of the ablation instrument against the biological tissue to be ablated, the support face defining an orifice in communication with a vacuum source. The method further includes creating a hermetic seal between the support face and the contacted biological tissue through the vacuum source to secure the ablating element in contact with the biological tissue; and ablating the biological tissue with the ablation element.

BRIEF DESCRIPTION OF THE DRAWINGS

The assembly of the present invention has other objects and features of advantage which will be more readily apparent from the following description of the best mode of carrying out the invention and the appended claims, when taken in conjunction with the accompanying drawing, in which:

FIG. 1 is a diagrammatic top plan view, in cross-section, of a microwave ablation instrument system with a directional reflective shield assembly constructed in accordance with one embodiment of the present invention.

FIG. 2 is an enlarged, fragmentary, top perspective view of the shield assembly of FIG. 1 mounted to an antenna assembly of the ablation instrument system.

FIG. 3 is a side elevation view, in cross-section, of the shield assembly of FIG. 2.

FIG. 4 is a front elevation view of the shield assembly taken substantially along the plane of the line 4—4 in FIG. 3.

FIGS. 10A and 10B are, respectively, bottom plan and side elevation views, partially broken away, of the securing apparatus of FIG. 8 having a pair of deformable suction-type cups, in accordance with one embodiment of the present invention.

FIGS. 11A and 11B are respectively, fragmentary, bottom plan and side elevation views, in partial cross-section, of an alternative embodiment securing apparatus having a fastener member for mounting to the shield assembly.

FIG. 12 is an end view, in cross-section, of the base support taken substantially along the plane of the line 12—12 in FIG. 11B.

FIG. 13 is a bottom plan view, in partial cross-section, of an alternative embodiment securing apparatus having a plurality of orifices, in accordance with one embodiment of the present invention.

FIG. 14 is a flow diagram of the relevant steps involved in securing an ablation element of the ablation instrument to a biological tissue to be ablated in accordance with one embodiment of the present invention.

DETAILED DESCRIPTION OF THE INVENTION

Figure 5:
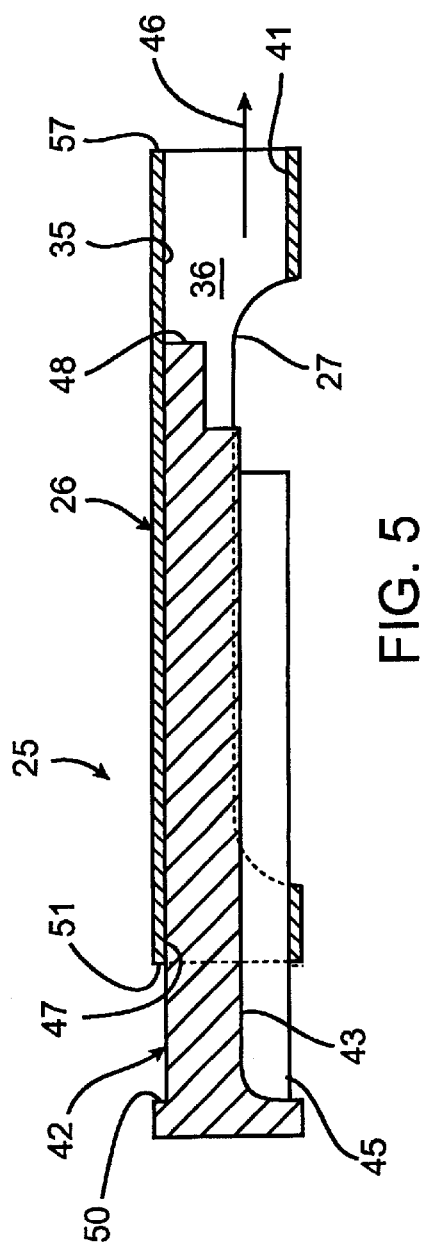
FIG. 5 is an exploded, side elevation view, in cross-section, of the shield assembly of FIG. 2, illustrating sliding receipt of an insert device in a cradle device of the shield assembly.

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various FIGURES.

Turning now to FIGS. 1 and 2, a microwave ablation instrument, generally designated 20, is provided which includes a transmission line 21 having a proximal portion 22 suitable for connection to an electromagnetic energy source (not shown), and an antenna 23 coupled to the transmission line 21 for radially generating an electric field sufficiently strong to cause tissue ablation. A shield assembly, generally designated 25, is coupled to the antenna 23 to substantially shield a peripheral area immediately surrounding the antenna from the electric field radially generated therefrom while permitting a majority of the field to be directed generally in a predetermined direction.

More specifically, a directional reflective shield assembly 25 is provided for a microwave ablation instrument including a cradle device 26 disposed about the antenna 23 in a manner substantially shielding a surrounding area of the antenna from the electric field radially generated therefrom. The cradle device 26 further provides a window portion 27 communicating with the antenna 23 which is strategically located relative the antenna to direct a majority of the field generally in a predetermined direction.

Accordingly, the shield assembly of the present invention enables predetermined directional transmission of the electric field regardless of the radial transmission pattern of the antenna. Tissue ablation can thus be more strategically controlled, directed and performed without concern for undesirable ablation of other adjacent tissues which may otherwise be within the electromagnetic ablation range radially emanating from the antenna. In other words, any other tissues surrounding the peripheral sides of the antenna which are out of line of the window portion of the cradle will not be subjected to the directed electric field and thus not be ablated. This ablation instrument assembly is particularly suitable for ablation procedures requiring accurate tissue ablations such as those required in the MAZE III procedure above-mentioned.

It will be appreciated that the phrase "peripheral area immediately surrounding the antenna" is defined as the immediate radial transmission pattern of the antenna which is within the electromagnetic ablation range thereof when the shield assembly is absent.

Transmission line 21, which is supported within a tubular shaft 31, is typically coaxial, and coupled to a power supply (not shown) which is external to instrument 20. As best illustrated in FIGS. 2 and 3, the microwave ablation instrument 20 generally includes an antenna 23 with a proximal end 28 and a distal end 30. The proximal end 28 of antenna 23 is grounded to an outer conductor (not shown) of transmission line 21. The distal end 30 of antenna 23 is attached to center conductor 32 of transmission line 21. Typically, antenna 23 is helical or in the form of a coil, i.e. an antenna coil, which is made from any suitable material, such as spring steel, beryllium copper, or silver-plated copper. However, the antenna may be any other configuration, such as a monopole, or a lossy transmission line. The connection between the antenna 23 and center conductor 32 may be made in any suitable manner such as soldering, brazing, ultrasonic welding or adhesive bonding. In other embodiments, the antenna 23 can be wound from the center conductor of the transmission line itself. This is more difficult from a manufacturing standpoint but has the advantage of forming a more rugged connection between the antenna and center conductor.

The outer diameter of antenna coil 23 will vary to some extent based on the particular application of the instrument. By way of example, a instrument suitable for use in an atrial fibrillation application may have typical coil outer diameters in the range of approximately 0.07 to 0.10 inches. More preferably, the outer diameter of antenna coil 23 may be in the range of approximately 0.08 to 0.09 inches.

The actual number of turns of the antenna coil may vary a great deal in accordance with the needs of a particular system. Some of the factors that will dictate the number of turns used include the coil diameter and pitch, the desired length of the lesion, the antenna configuration, the instrument diameter, the frequency of the electromagnetic energy, the desired field strength and the power transfer efficiency within the tissue. Moreover, since these coiled antennas are preferably filled or cast with a silicone insulator to insulate each coil from one another and from the center conductor, the pitch of the coils can be smaller and the number of turns increased. In MAZE III applications, for example, the antenna is comprised of about thirty-seven (37) turns, and has a length in the range of approximately 19.8 mm to 20.0 mm. The antenna is typically spaced at least 0.5 mm, as for example in the range of approximately 0.5 to 2.0 mm, from the distal end of the transmission line shield (not shown) and at least approximately 0.5 mm, as example in the range of approximately 0.5 to 1.0 mm from the distal end of the transmission line dielectric 33.

To substantially reduce or eliminate electromagnetic radiance of the distal end of the transmission line 21, the antenna is fed at its resonance frequency to better define the electromagnetic field along the coil. The antenna is preferably tuned by adjusting the length and the number of turns of the coil so that the resonance frequency of the radiative structure is in the range of about 2.45 GHz, for example. Consequently, the energy delivery efficiency of the antenna is increased, while the reflected microwave power is decreased which in turn reduces the operating temperature of the transmission line. Moreover, the radiated electromagnetic field is substantially constrained from the proximal end to the distal end of the antenna. Thus, when a longitudinally extending coil is used, the field extends substantially radially perpendicularly to the antenna and is fairly well constrained to the length of the antenna itself regardless of the power used. This arrangement serves to provide better control during ablation. Instruments having specified ablation characteristics can be fabricated by building instruments with different length antennas.

Briefly, the power supply (not shown) includes a microwave generator which may take any conventional form. When using microwave energy for tissue ablation, the optimal frequencies are generally in the neighborhood of the optimal frequency for heating water. By way of example, frequencies in the range of approximately 800 MHz to 6 GHz work well. Currently, the frequencies that are approved by the U.S. Food and Drug Administration for experimental clinical work are 915 MHz and 2.45 GHz. Therefore, a power supply having the capacity to generate microwave energy at frequencies in the neighborhood of 2.45 GHz may be chosen. At the time of this writing, solid state microwave generators in the 1–3 GHz range are very expensive. Therefore, a conventional magnetron of the type commonly used in microwave ovens is utilized as the generator. It should be appreciated, however, that any other suitable microwave power source could be substituted in its place, and that the explained concepts may be applied at other frequencies like about 434 MHz, 915 MHz or 5.8 GHz (ISM band).

Referring back to FIGS. 2 and 3, the shield assembly of the present invention will be described in detail. In accordance with the present invention, cradle device 26 defines a window portion 27 strategically sized and located to direct a majority of the electromagnetic field generally in a predetermined direction. Cradle device 26 is preferably tubular or cylindrical-shell shaped having an interior wall 35 defining a cavity 36 extending therethrough which is formed for receipt of the antenna 23 therein. While the cradle device is shown and described as substantially cylindrical-shaped along the longitudinal and cross-section dimensions, it will be appreciated that a plurality of forms may be provided to accommodate different antenna shapes or to conform to other external factors necessary to complete a surgical procedure. For example, by longitudinally curving the antenna, either through manual bending or through manufacture, a curvilinear ablative pattern may be achieved. Such a configuration, by way of example, may be necessary when ablating tissue around the pulmonary veins in the MAZE III procedure.

Cradle device 26 is preferably thin walled to minimize weight addition to the shield assembly, while being sufficiently thick to achieve the appropriate microwave shielding as well as provide the proper mechanical rigidity to the antenna area. In the preferred embodiment, cradle device 26 is composed of a conductive, metallic material which inherently functions as a reflector. The walls of the cradle device, therefore, are substantially impenetrable to the passage of microwaves emanating from the antenna. Moreover, a percentage of microwaves may be reflected them back into the cavity 36, and subsequently remitted out of window portion 27. One particularly suitable material is stainless steel, for example, having a thickness in the range of about 0.010 inches to about 0.025 inches, and more preferably about 0.015 inches.

As mentioned, an elongated helical microwave antenna normally emits an electromagnetic field substantially radially perpendicular to the antenna length which is fairly well constrained to the length of the coil regardless of the power used. Accordingly, the proximal and distal ends of the cradle may not require shielding by the cradle device in the same manner as that required radially perpendicular to the longitudinal axis of the antenna.

As best viewed in FIGS. 4 and 5, window portion 27 preferably radially extends through one side of the cradle and into the cavity 36, and further extends longitudinally along cradle in a direction substantially parallel to the longitudinal axis thereof. The length of the ablative radiation is therefore generally constrained to the length of the coil, and may be adjusted by either adjusting the length of the antenna (a helical antenna for example), or by adjusting the longitudinal length of the window portion 27. To maximize efficiency, however, the length of the window portion 27 is generally a little longer than the longitudinal length of the antenna 23, by about 1–2 mm on each side. This allows reflections out of the window portion. It will be appreciated, however, that the window portion may be collectively defined by a plurality of sections (not shown), or that the cradle device may include more than one strategically positioned window portion.

For a tubular cradle device 26, FIG. 4 illustrates that the circumferential opening of the window portion 27 may extend circumferentially from about 45° to about 180°, and most preferably extend circumferentially about 160°. A substantial portion of the backside of the antenna, therefore, is shielded from ablative exposure of the microwaves radially generated by the antenna in directions substantially perpendicular to the longitudinal axis 37 thereof. The circumferential dimension of window portion 27, hence, may vary according to the breadth of the desired ablative exposure without departing from the true spirit and nature of the present invention.

Accordingly, the predetermined direction of the ablative electromagnetic field radially generated from the antenna may be substantially controlled by the circumferential opening dimension, the length and the shape of the cradle window portion 27. Manipulating the positioning of window portion 27 in the desired direction, thus, controls the direction of the tissue ablation without subjecting the remaining peripheral area immediately surrounding the antenna to the ablative electromagnetic field.

Briefly, ablation instrument 20 includes a handle 38 coupled to the antenna and the cradle device 26 through an elongated tubular shaft 31. By manually manipulating the handle, the cradle window portion 27 may be oriented and positioned to perform the desired ablation. The shaft is preferably provided by a metallic hypotube which is mounted to the metallic cradle device through brazing paste, welding or the like. Moreover, the shaft 31 is preferably bendable and malleable in nature to enable shape reconfiguration to position the antenna and the cradle device at a desired orientation relative the handle. This enables the surgeon to appropriately angle the window portion toward the targeted region for tissue ablation. It will be appreciated, however, that the material of the shaft is further sufficiently rigid so that the shaft is not easily deformed during operative use. Such materials, for example, includes stainless steel or aluminum having diameters ranging from about 0.090 inches to about 0.200 inches with wall thickness ranging from about 0.050 inches to about 0.025 inches. Most preferably, the shaft is 304 stainless steel having an outer diameter of about 0.120 inches and a wall thickness of about 0.013 inches.

The resonance frequency of the antenna is preferably tuned assuming contact between the targeted tissue and the longitudinal dimension of the antenna 23 exposed by the window portion 27. Hence, should a portion of, or substantially all of, the exposed region of the antenna not be in contact with the targeted tissue during ablation, the resonance frequency will be adversely changed and the antenna will be untuned. As a result, the portion of the antenna not in contact with the targeted tissue will radiate the electromagnetic radiation into the surrounding air. The efficiency of the energy delivery into the tissue will consequently decrease which in turn causes the penetration depth of the lesion to decrease.

Thus, tissue contact with the antenna is best achieved placing and orienting the antenna longitudinally adjacent and into the cradle window portion 27, as viewed in FIGS. 3 and 4. The longitudinal axis 37 of the antenna is thus off-set from, but parallel to, the longitudinal axis 40 of cradle device 26 in a direction toward the window portion. In this regard, the antenna may generally be positioned closer to the area designated for tissue ablation. Moreover, by positioning the antenna actively in the window portion 27 of the cradle device, the transmissive power of the antenna may be effected substantially along the full circumferential opening of the window portion 27.

This arrangement of positioning the antenna actively in the cradle window portion 27 is partially achieved by mounting a distal portion of shaft 31 in alignment with the window portion, and to an interior wall 35 of cradle device 26. As shown in FIG. 3, the distal end of the shaft 31 extends through a proximal opening 41 into cavity 36 of the cradle device 26 which initially positions the longitudinal axis of the shaft and that of the cradle device substantially parallel one another. It will be appreciated, however, that these axes need not be parallel.

To maintain the electromagnetic field characteristics of the antenna during operative use, it is imperative to stabilize the position of antenna 23 relative the cradle device 26. Relative position changes or antenna deformation may alter the resonant frequency of the antenna, which in turn, changes the field characteristics of the antenna. Accordingly, to stabilize the antenna 23 relative the cradle device 26, the shield assembly 25 further includes an insert device, generally designated 42, disposed in cradle device cavity 36 between the cradle device and the antenna.

Insert device 42 includes a longitudinally extending recess 43 formed and dimensioned for press-fit receipt of the antenna therein. In accordance with the present invention, the recess 43 is preferably cylindrical shaped and extends substantially longitudinally along a surface of the insert device. This configuration positions, stabilizes and retains the helical antenna 23 actively in the window portion 27 to maximize exposure of the targeted tissue to the microwaves generated by antenna. The recess 43 further includes a directional port 45 communicating with the recess 43 which aligns the same with the window portion 27 of the cradle device 26 to direct the majority of the field generally in the predetermined direction. For a curvilinear antenna, it will be understood that the recess may be similarly conformed.

The insert device 42 further performs the function of decreasing the coupling between the antenna 23 and the metallic cradle device 26. Should the antenna be too close to the metallic surface of the cradle device, a strong current may be induced at the surface thereof. This surface current will increase the resistive losses in the metal and the temperature of the cradle device will increase. On the other hand, direct conductive contact or substantially close contact of the antenna with the metallic cradle device will cause the reflective cradle device to become part of the radiative structure, and begin emitting electromagnetic energy in all directions.

Insert device 42 is therefore preferably provided by a good dielectric material which is relatively unaffected by microwave exposure, and thus capable of transmission of the electromagnetic field therethrough. Preferably, this material is provided by a low-loss dielectric material such as TEFLON, silicone, or polyethylene, polyimide, etc.

Insert device 42 is preferably provided by a substantially solid cylindrical structure dimensioned for a sliding interference fit, in the direction of arrow 46 (FIG. 5), through a distal opening 47 of the cradle device cavity 36. Thus, the outer diameter of the insert device is preferably slightly larger than the inner diameter of the cavity 36 defined by cradle interior wall 35. A proximal portion of insert device 42 includes a semicircular alignment tongue 48 formed to cooperate with the distal end of the shaft 31 during sliding receipt of the insert device 42 in the cradle device 26 for alignment thereof. Moreover, a distal portion of the insert device 42 includes an annular shoulder portion 50 formed and dimensioned to contact a distal edge 51 of cradle device 26 upon full insertion of insert device into cavity 36. Collectively, the alignment tongue 48 and the annular shoulder portion 50 cooperate to properly align the recess 43 and the directional port 45, and thus the press-fit antenna 23, in the window portion 27 of the cradle device. Moreover, for reasons to be discussed henceforth, the circumferential dimension of the shoulder portion 50 is conformed substantially similar to that of the cradle device (FIG. 3).

By composing the cradle device 26 of a high conductivity metal, a superior microwave reflector is produced. Thus, when an electromagnetic wave originating from the antenna reaches the cradle device, a surface current is induced. That current will in turn generate a responsive electromagnetic field that will interfere with the incident field in such a way that the total electromagnetic field in the cradle device will be negligible.

While a majority of the electromagnetic energy is reflected by the metallic cradle device 26, since it is not a perfect conductor, a fraction of the incident electromagnetic energy is absorbed by resistive losses therein. Consequently, the cradle device 26 itself may eventually generate heat in an amount detrimental to the surrounding tissue. The shield assembly 25 of the present invention, therefore, preferably includes an insulator 52 disposed about the cradle device 26 to insulate the surrounding tissues from the cradle device. As best viewed in FIGS. 2–4, insulator 52 is disposed peripherally about the cradle device 26 in a manner conductively contacting the outer surface thereof and particularly substantially along its length dimension.

The insulator 52 provides a longitudinally extending bore 53 formed and dimensioned for sliding receipt of the cradle device 26 therein. Preferably, such sliding receipt is performed through an interference fit to insure conductive contact between the insulator and the cradle device. Accordingly, the insulator 52 further performs the function, in part, of a heat sink for the transfer and dissipation of heat into the insulator 52 from the cradle device 26.

Similar to the insert device 42, the insulator 52 defines a directional window 55 extending into the bore 53 from a side wall thereof. This directional window 55 is aligned to communicate with the window portion 27 of the cradle device 26 and the directional port 45 of the insert device 42 so that the cradle device can direct the majority of the field generally in the predetermined direction. Preferably, as viewed in FIG. 4, the directional window 55 of the insulator 52 is circumferentially dimensioned slightly smaller than or substantially equal to the circumferential dimension of the window portion 27 of cradle device 26. This arrangement minimized exposure of the edges defining the window portion 27 to tissues during operation.

To appropriately cool the cradle device during operational use, the insulator 52 must be designed with a sufficient heat transfer capacity to transfer and dissipate the heat continuously generated by the cradle device. One factor determining both the insulatory and heat sink capacity is the material composition. The insulator material, however, preferably has a low losstangent and low water absorption so that it is not itself heated by the microwaves. In accordance with the present invention, the insulator is preferably provided by a suitable thermoplastic material such as ABS plastic.

The other primary factor determining the heat sink capacity is the volume of the insulator contacting the cradle device. FIGS. 3 and 4 best illustrate that the insulator 52 is preferably substantially cylindrical-shaped in conformance with the peripheral dimensions of the cradle device 26. The longitudinal axis of bore 53 is off-set from that of the insulator 52 which functions to position the antenna 23 in the aligned windows, and collectively closer to tissues targeted for ablation. Moreover, a backside of the insulator 52 is substantially thicker and more voluminous than the opposed frontside thereof which defines the directional window 55. This configuration provides greater heat sink capacity at the backside of the insulator 52 which conductively contacts a substantial majority of the backside of cradle device 26.

Bore 53 preferably includes a distal opening 58 therein which is formed for sliding receipt of the substantially uniform transverse cross-sectional dimension of the cradle device 26. Sliding support of the insulator 52 longitudinally along the cradle device 26 continues until a back wall 56 of the bore 53 contacts the proximal edge 57 of the cradle device 26. This functions to limit the insertion of the cradle device 26 in the bore 53. At the distal end portion of the insulator 52, the annular shoulder portion 50 of the insert device 42 slideably contacts the interior wall of the bore distal opening 58 to secure the insulator to the cradle device and the insert device. The circumferential dimension of the shoulder portion 50 is preferably dimensioned to provide an interference fit with the shoulder portion. Thus, the outer diameter of the shoulder portion 50 is preferably slightly larger than the inner diameter of the bore 53 of the insulator 52. An adhesive, such as cyanoacrylate, may be applied to further secure the insulator in place.

As shown in FIGS. 2 and 3, once the insulator is properly positioned, the distal end thereof is dimensioned to be positioned substantially flush with the distal end of the insert device 42. Further, the insert device 42 and the insulator 52 cooperate to enclose the distal edge 51 of the cradle device therein.

Figure 6:
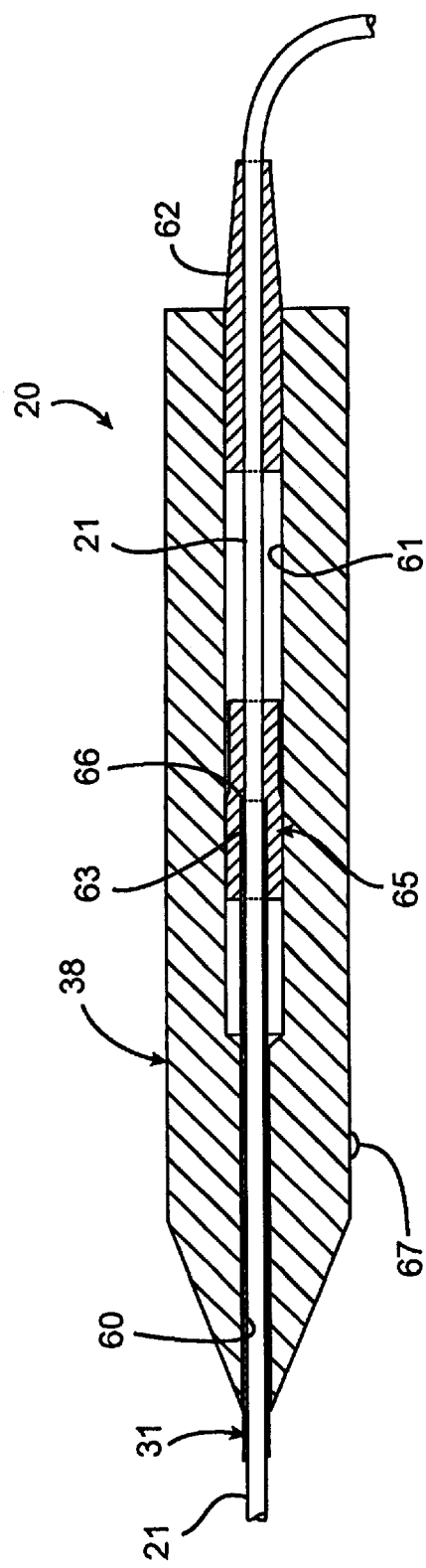
FIG. 6 is a fragmentary, side elevation view, in cross-section, of a handle of the ablation instrument system of the present invention.

Referring now to FIG. 6, a handle 38 for the ablation instrument 20 will be described in detail. In the preferred form, the handle 38 is composed of a nonconductive, relatively rigid material, such as ABS plastic. As above-indicated, the handle 38 is provided as a vehicle to manually manipulate the orientation and positioning of the cradle window portion 27 during operational use. This is performed by rigidly attaching the handle to a proximal end portion of the shaft 31.

At a distal portion of the handle 38, a passage 60 extends axially into an interior portion of the handle. The diameter of the passage 60 is preferably substantially equal to the shaft diameter to minimize the tolerance therebetween. An interior wall 61 of the handle portion defines an axially extending cavity 36 which communicates with the distal passage 60. The cavity 36 is preferably of a diameter larger than that of the passage 60, and preferably extends through handle 38 substantially coaxial with the passage 60.

The shaft is positioned in the handle passage 60 such that the shaft proximal end terminates in the cavity 36. To rigidly mount the shaft 31 to the handle 38, an insert screw (not shown) or the like, or an adhesive may be applied in the passage between the shaft 31 and the handle 38.

As shown in FIG. 6, the transmission line 21 extends through the proximal cavity 36 and into the tubular shaft for coupling to the antenna 23. An elastic retraining device 62 may be provided mounted in the cavity 36 at the proximal end of the handle which cooperates with the transmission line 21 to mount the same to the handle.

Due to the conductive nature of the metallic hypotube or tubular shaft 31 and the coaxial arrangement between outer conductor of the coaxial cable and the metallic shaft, a second transmission line is formed between these substantially concentric cylindrical metallic surfaces. Electromagnetic energy emitted by the antenna excites this second transmission line which detrimentally propagates microwave energy between metallic tube and the outer conductor of the coaxial cable. Thus, a part of the microwave energy is propagated back toward the handle.

In accordance with the present invention, handle 38 further includes a microwave absorbent 65 disposed peripherally around the proximal portion of the tubular shaft 31 to substantially absorb microwave radiation transmitted by the proximal end thereof. While the microwave absorbent may be integrally formed in the materials composing the handle, it is preferred that a material 65 containing the microwave absorbent be disposed or wrapped about the juncture 66 between proximal end 63 of the shaft 31 and transmission line 21, as shown in FIG. 6.

In the preferred embodiment, this material wrap 65 is a silicon based microwave absorbent, such as C-RAM KRS-124 from Cuming Microwave Corp. having a thickness of about 0.085 inches. Moreover, this material wrap 65 must be sufficient in length to extend over the juncture 66 between the shaft proximal end 63 and the transmission line 21. Preferably, the wrap extends equidistant from the juncture 66 in each direction by about 0.25 inches to about 0.75 inches. This distance may vary depending upon the anticipated amount of electromagnetic field transmission, the material thickness and the type of microwave absorbent applied.

In accordance with the present invention, to facilitate location of the window portion 27 relative the handle 38 during operative use, a marking device 67 and method are provided. Such location marking is particularly useful during operative use when the antenna and shield assembly cannot be easily viewed.

Preferably, a visual or tactile marking device 67 (FIG. 6) is located along the handle 38 to communicate to the surgeon the location and orientation window portion. This visual marking may be provided by a simple depression mark, painted mark or illuminated mark, or the like easily viewed along the handle. This marking is preferably positioned and aligned in a plane bisecting the window portion 27 and the handle 38. More preferably, as shown in FIG. 6, the marking is positioned on the same side of the handle as the window portion 27. However, it will be understood that the marking may be placed anywhere along the handle 38 as long as the position thereof remains affixed relative the window portion.

Although only a few embodiments of the present inventions have been described in detail, it should be understood that the present inventions may be embodied in many other specific forms without departing from the spirit or scope of the inventions. Particularly, the invention has been described in terms of a microwave ablation instrument for cardiac applications, however, it should be appreciated that the described small diameter microwave ablation instrument could be used for a wide variety of non-cardiac ablation applications as well. The size and pitch of the described antenna coils may be widely varied. It should also be appreciated that the longitudinally oriented antenna coil does not need to be strictly parallel relative to the shaft axis and indeed, in some embodiments it may be desirable to tilt the antenna coil somewhat. This is especially true when the malleable shaft is reconfigured to the particular needs of the surgical application. The antenna can also be flexible and malleable.

It should also be appreciated that the microwave antenna need not be helical in design. The concepts of the present invention may be applied to any kind of radiative structure, such as a monopole or dipole antennas, a printed antenna, a slow wave structure antenna, a lossy transmission line or the like. Furthermore, it should be appreciated that the transmission line does not absolutely have to be a coaxial cable. For example, the transmission line may be provided by a stripline, a microstrip line, a coplanar line, or the like.

The conventional technique employed to position and ablate the biological tissue with the ablation instrument has been to manually hold the handle of the ablation instrument in a manner causing the ablating element to contact against the targeted area. For the most part, whether or not the ablating element is in contact with the targeted tissue, has been determined by the surgeon's skill and experience with the aid of imaging technology. The ablation device, however, is typically hard to manipulate (e.g., user steadiness and moving tissues) and frequently requires repositioning to ensure that the targeted area is being properly ablated. During a cardiac ablation procedure, for example, the heart may be moving away from the ablation element by as much as 1 cm. Consequently, it is fairly difficult to maintain continuous contact between the ablation element and the heart during these cardiac procedures.

Figure 7:
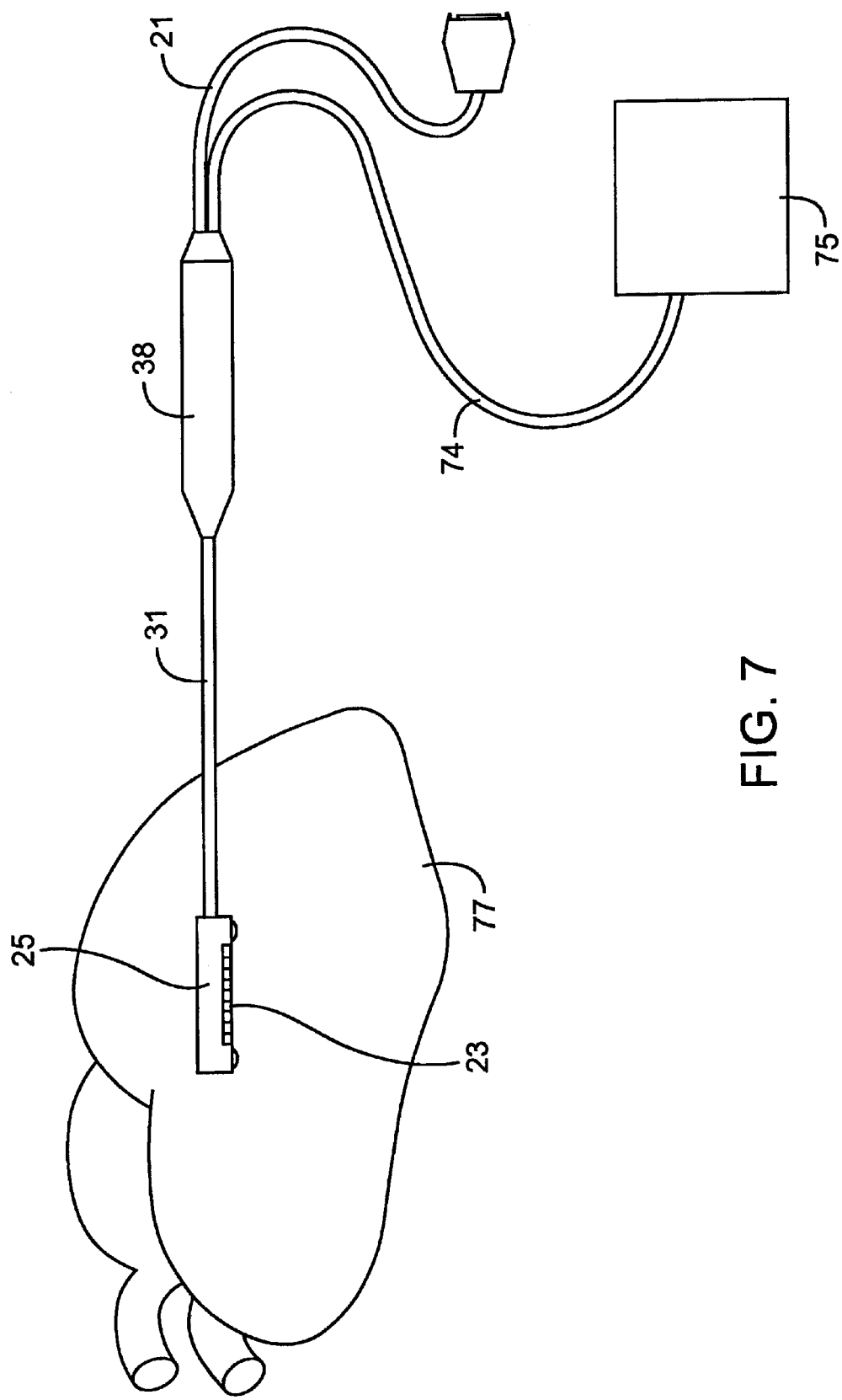
FIG. 7 is a diagrammatic side elevation view of a microwave ablation instrument system secured to a biological tissue with a securing apparatus constructed in accordance with one embodiment of the present invention.

In view of above, it is desirable to provide an ablation instrument that facilitates continuous contact with the targeted biological tissue during the ablation procedure. As best viewed in FIGS. 7–9 a securing apparatus, generally designated 68, is provided for selectively securing an ablation element 23 of an ablation instrument 20 proximate to a targeted region of a biological tissue.

The securing apparatus 68 includes a support base 69 having a support face 70 which is adapted to seat against the biological tissue proximate to the ablation element 23. The support face further defines a passage 72 having one end communicably coupled to a vacuum source 75 and an opposite end terminating at an orifice 76 at the support face. During the operation of the vacuum source 75, and while the orifice 76 is substantially positioned against the biological tissue 77 (FIG. 7), the support face 70 is caused to form a hermetic seal with the biological tissue to secure the ablation instrument thereto. Thus, the securing apparatus facilitates the maintenance of continuous contact of the ablation element against the targeted biological tissue to produce a more strategically positioned lesion.

Accordingly, upon proper manipulation and positioning of the ablation element against targeted biological tissue, the orifices of the securing apparatus will be moved to an orientation seated adjacent the targeted tissue. The securing apparatus 68 may then be activated to generate a vacuum at the orifices 76', 76". In turn, the ablation element can be continuously secured against the targeted tissue for the duration of the ablation.

Briefly, the ablation instrument 20 is, for example, preferably provided by the ablation instrument illustrated in FIGS. 1–3. As previously described, the ablation instrument 20 includes a transmission line 21, an antenna ablating element 23, a shield assembly 25, a shaft 31, and a handle 38, which respectively communicate to direct a majority of the field generally in a predetermined direction.

In accordance with one embodiment of the present invention, the securing apparatus 68 is configured to be integrally formed with the shield assembly 25 of the ablation instrument 20. In this configuration, the support base 69 of the securing apparatus 68 is integrally formed with the cradle device 26 of the shield assembly 20. However, as will be discussed in greater detail below, the support base may also be configured to be independent from the shield assembly (e.g., as a separate member coupled to a portion of the shield assembly as shown in FIGS. 11A and 11B, or by replacing the shield assembly entirely).

Correspondingly, the support base 69 may be disposed about the antenna 23 such that the support floor 70 substantially surrounds the outer periphery of the antenna and forms window portion 27. Preferably, the support base is adjacent to the antenna to promote stability of the securement and to enable the antenna element to be as close to the biological tissue as possible. As described, the window portion 27 is strategically located relative to the antenna 23 and configured to cooperate with the antenna 23 to direct a majority of the field generally in a predetermined direction.

Figure 8:
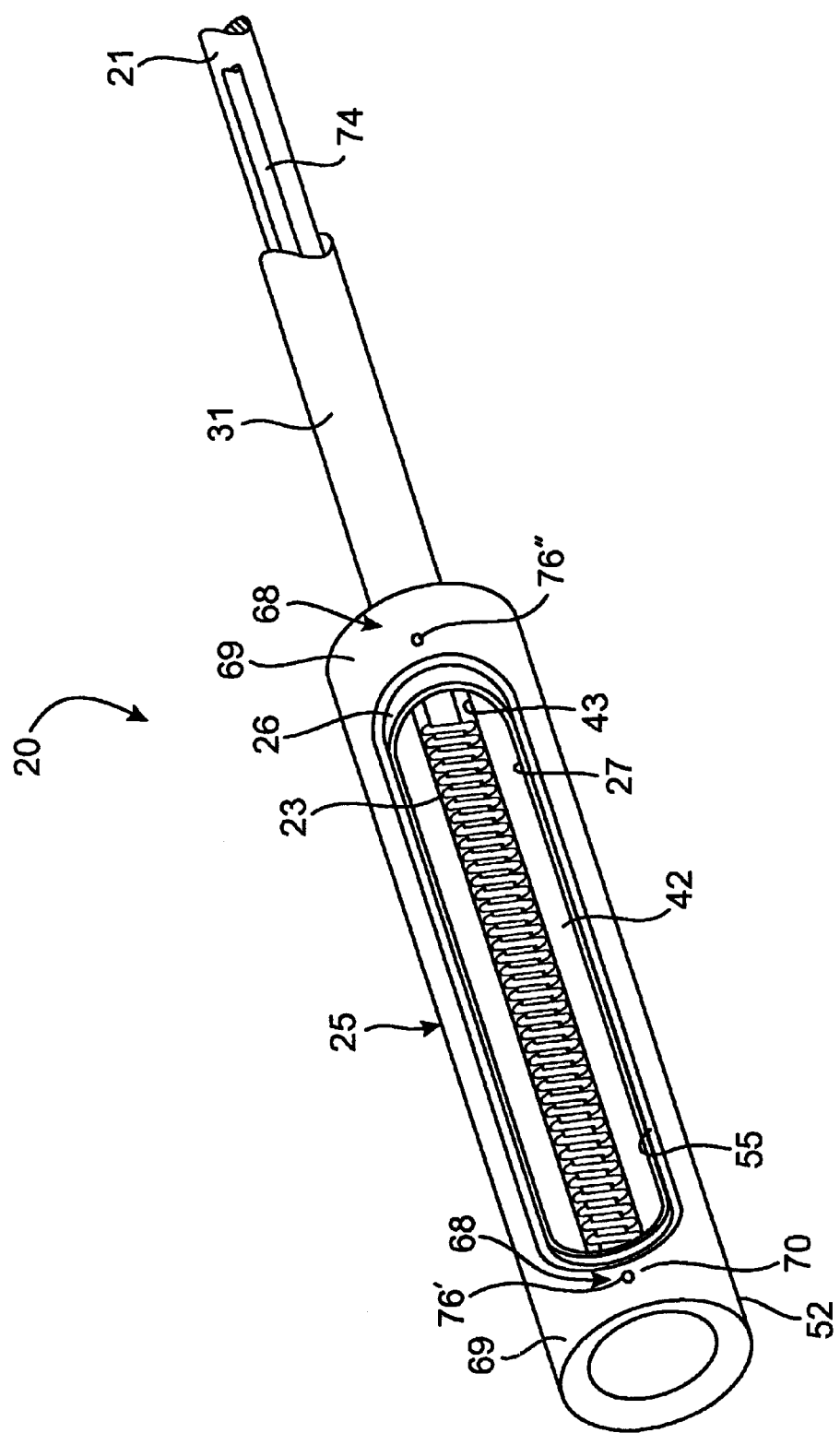
FIG. 8 is an enlarged, fragmentary, top perspective view of the antenna assembly of the ablation instrument system incorporating the securing apparatus of FIG. 7.

The support base 69, which in this embodiment is integral with the cradle device 26, defines a passage 72 having one end communicably coupled to a fluid line 74 and an opposite end terminating at an orifice 76 at the support face 70. Thus, fluid line 74 is communicably coupled to passage 72. Preferably, the proximal end of the fluid line 74 is operatively coupled to a vacuum source 75, which generates the vacuum necessary to secure the ablating instrument to the biological tissue. The fluid line is preferably provided by a relatively thin diameter flexible Teflon tube of sufficient wall thickness to prevent collapse under the vacuum, (e.g., medical grade). As shown in FIG. 8, the fluid line 74 is preferably disposed inside the tubular shaft 31 of the ablation instrument 20 to minimize the collective diameter thereof. In the preferred form, therefore, the fluid line 74 extends through the shaft 31 and into the support base 69 for coupling to the passage 72. It will be appreciated, however, that the fluid line may be disposed external to the shaft 31 as well. It will also be appreciated that the vacuum lines can be independently connected to the vacuum source 75.

Briefly, the vacuum supply 75 includes a vacuum generator, which may take any conventional form, such as a vacuum pump or a venturi vacuum generator (e.g. powered by a pressurized air or water supply). Furthermore, the vacuum generator may be part of the internal vacuum supply system of a hospital or an external stand alone unit in the operating room. In the preferred embodiment, the vacuum generator produces a vacuum in the range of about 30 mm Hg to about 60 mm Hg for a pair of spaced-apart orifices 76', 76" having a diameter of about 1–2 mm. It should be appreciated, however, that any other suitable vacuum supply may be employed, and that other vacuum ranges may apply depending upon the size of the orifice.

Figure 9:
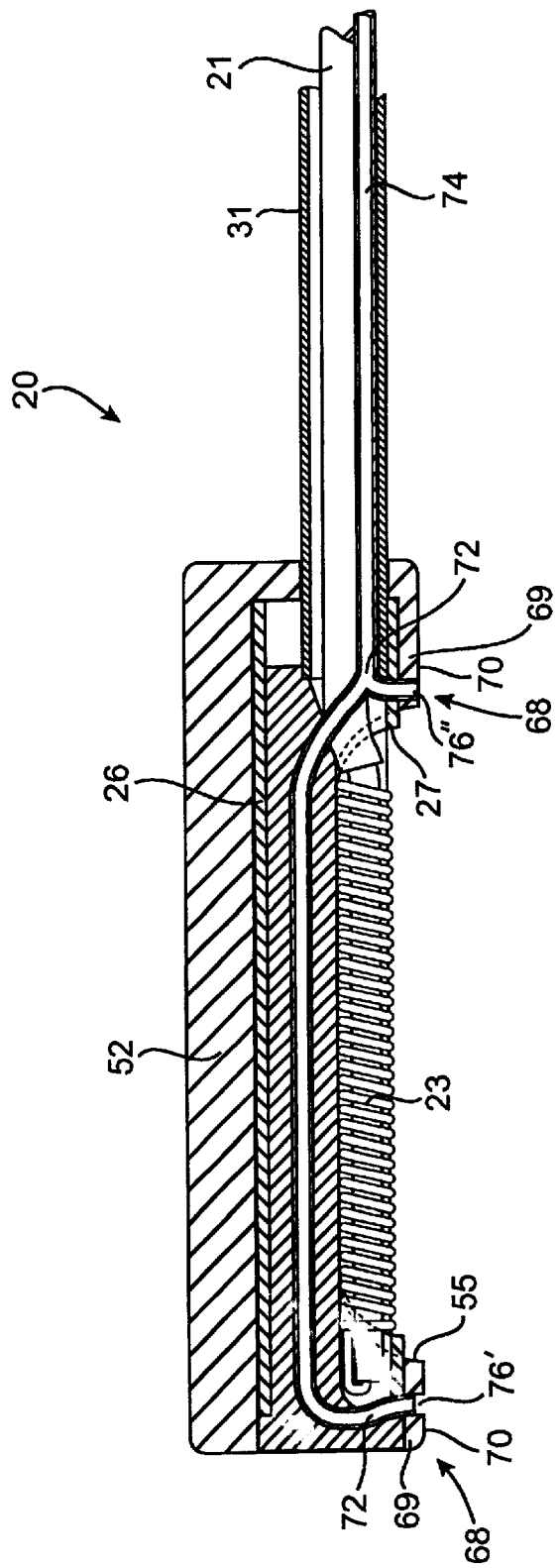
FIG. 9 is an enlarged, fragmentary, side elevation view, in cross-section, of the securing apparatus of FIG. 8.

FIGS. 8 and 9 best illustrate that the proximal orifice 76' is positioned on a proximal end of the window portion 27 while the distal orifice 76" is positioned on a distal end thereof. Preferably, the orifices are disposed proximate to the antenna, and on opposite ends of the window portion. This arrangement best maintains securement to the targeted tissue, and thus the antenna alignment, when the securement apparatus 68 is activated during ablation. As will be described in greater detail below and as shown in FIG. 13, the securing apparatus may include a plurality of orifices 76 spaced-apart peripherally around window portion 27, or may be provided a single strategically positioned orifice (not shown).

As set forth above, the vacuum force necessary to anchor the ablation device to the tissue is dependent upon the geometry and transverse cross-sectional dimension of the orifices. Therefore, these parameters are configured to have the smallest cross-sectional dimension, relative to the vacuum force, yet provide sufficient securement of the support face against the biological tissue without damage thereto. Additionally, the orifice is sized to maintain the integrity of the hermetic seal between the support face and the biological tissue. Preferably, the orifices have a diameter in the range of about 1–2 mm for a vacuum source of about 30–60 mm Hg (at the orifices 76' and 76").

The support face 70 is further adapted to seat against the biological tissue proximate to the antenna 23 and in a manner forming a hermetic seal against the biological tissue during operation of the vacuum source. This is performed by providing a support face which is relatively smooth and non-porous which facilitates sealing against the tissue. While the support face is shown as smoothly curved (i.e., cylindrical) along the longitudinal and cross section dimensions, it will be appreciated that a plurality of forms may be provided to accommodate external factors necessary to complete a surgical procedure. For example, the shape of the support face may be configured to coincide with the shape of the biological tissue to further promote sealing.

Preferably, the support face 70 is dimensioned to vertically align the ablation element 23 against the targeted tissue. This contact ensures that the majority of the electromagnetic field generated is directed into the targeted tissue without subjecting the immediate peripheral area surrounding the ablating element to the ablative electromagnetic field. In this manner, the ablation element will effectively and efficiently ablate the targeted biological tissue.

In one embodiment of the invention, the support face 70 may be composed of a soft deformable material which is relatively firm yet can substantially conform to the surface of the targeted biological tissue. Such confirmation maintains seal integrity between the securing apparatus and the biological tissue so that a vacuum loss is less likely during the ablation procedure. For example, as shown in FIG. 10, the support face may include a pair suction cups 80', 80", communicably coupled to the orifices 76' and 76". For the most part, a standard connection used to couple the suction cups 80', 80" to the orifices 76', 76". Upon application of the vacuum source the suction cups engage and conform to the contacting tissue for seal formation therebetween.

In an alternative embodiment of the present invention, the securing apparatus 68 is adapted to be retrofit to the shield assembly 25 of FIGS. 1–6. In this embodiment, referring now to FIGS. 11A and 11B, the support base 69 of the securing apparatus 68 is removably coupled to a distal portion of the ablation instrument 20 through a fastening member 81. More particularly, this configuration removably mounts the securing apparatus 68 to the shaft 31 of the ablation instrument 20. As shown in FIG. 12, support base 69 defines an aperture 82 extending therethrough which is formed for receipt of shaft 31. Hence, the fastening member 81 may affix to shaft 31 through an interference fit therewith or through a bolt-type fastener (not shown). In the preferred form, the support base 69 is C-shaped (FIG. 11B) having opposed leg portions 83', 83" which extend around the shield assembly 25 and terminate at support faces 70', 70". Similar to the previous embodiment, these support faces are adapted to seat against the biological tissue during ablation to create a hermetic seal for the respective orifices 76', 76".

Furthermore, each leg portion 83', 83" of the support base 69 defines passages 72', 72" each having one end communicably coupled to a fluid line 74 and an opposite end terminating at a respective orifice 76', 76" at the support face 70', 70". As best illustrated in FIG. 12, passage 72' of leg portion 83' is adapted to extend around aperture 82 to avoid interference with the instrument shaft 31. While the retrofit embodiment of the present invention is illustrated as having opposed leg portions 83', 83", at the proximal and distal ends of the shield assembly 25, it will be appreciated that the support base may be disposed at only one of the distal end and the proximal end of the shield assembly or on the sides of the window portion 27 thereof.

In yet another alternative embodiment, the securing apparatus may include a plurality of spaced-apart orifices 76 peripherally extending around the window portion 27 of the securing apparatus (FIG. 13). This configuration enables a more secure mount to the biological tissue by providing additional orifices surrounding the ablation element 23. Preferably, a plurality of vacuum lines (not shown) are provided to ensure seal integrity of securing apparatus 68 in the event of leakage of one of the seals. For example, each vacuum line may be communicably coupled to 1–3 orifices. Thus, a vacuum leak at one of these orifices will not affect the seal integrity of the other vacuum lines. This multiple vacuum line concept may be applied to the other configurations as well. Alternatively, these orifices 76 may be communicably coupled to only one vacuum line.

In accordance with another aspect of the present invention, a method is provided for securing the ablation element 23 of ablation instrument 20 to a biological tissue 77 to be ablated. Referring now to the flow diagram of FIG. 14, conventional pre-ablation events may apply such as introducing the ablation instrument 20 into a patient's body to position the ablating element 23 of the ablation instrument 20 adjacent to the biological tissue to be ablated. These pre-ablation steps (step 100) are conventional and are readily understood by those skilled in the art.

Correspondingly, the first step 102 includes contacting the support face 70 of the support base 69 against the biological tissue to be ablated. Once the ablation instrument is in the proper position (e.g., proximate the targeted tissue), the securing apparatus 68 may be activated to secure the ablation instrument. Thus, at the second step 104, the method may include creating a hermetic seal between the support face 70 and the contacted biological tissue 77 with the vacuum source 75. By creating a hermetic seal, the ablating element (e.g., antenna) is secured to the biological tissue 77 in the desired direction.

After the ablation instrument 20 is secured to the tissue 77, the third step 106, of ablating the biological tissue with the ablation element 23 may commence. By securing the ablation instrument to the biological tissue, the ablation instrument is able to direct the majority of the field generally in the predetermined direction without subjecting the immediate peripheral area surrounding the ablating element to the ablative electromagnetic field.

After ablation the targeted biological tissue, the fourth step 108 may commence which involves reducing the vacuum and breaking the hermetic seal. This may be performed by simply pulling the ablation instrument away from the targeted tissue, or by reducing the vacuum through a pressure valve or the like.

It should be appreciated that additional ablating steps may be needed to complete the ablation procedure and therefore the foregoing steps may be used several times before ending the ablation procedure. Thereafter, conventional post-ablation steps (step 110) are performed that are well known to those skilled in the art and therefore, for the sake of brevity will not be discussed herein.

While this invention has been described in terms of several preferred embodiments, there are alterations, permutations, and equivalents which fall within the scope of this invention. It should also be noted that there are many alternative ways of implementing the methods and apparatuses of the present invention.

By way of example, the secured ablation instrument may be disengaged from the biological tissue with an air pulse. The fluid line may further be coupled to the transmission line to form one combination line, extending from the ablation instrument. Further still, the vacuum force may be adjustably controlled with a flow controller or the like. Additionally, vacuum sensors may be employed to continuously monitor the vacuum applied to secure the ablation instrument to the biological tissue.

It is therefore intended that the following appended claims be interpreted as including all such alterations, permutations, and equivalents as fall within the true spirit and scope of the present invention.

What is claimed is:

1. A securing apparatus for selectively securing an ablating element of an ablation instrument proximate to a targeted region of a biological tissue comprising:

a support base adapted to affix to said ablation instrument relative said ablating element, and having a support face adapted to seat against the biological tissue proximate to the ablation element, said support face defining a window portion configured to cooperate with the ablating element of the ablation instrument to direct a majority of an ablating field of the ablating element generally in a predetermined direction, said support base further defining a passage having one end communicably coupled to a vacuum source and an opposite end terminating at the support face at a proximal orifice positioned on a proximal end of said window portion, and at a distal orifice positioned on a distal end of said window portion; wherein said support face forms a hermetic seal against the biological tissue during operation of said vacuum source to secure the ablation instrument thereagainst.

2. A securing apparatus as defined in claim 1, further including a fastening member configured to couple the support base to the ablation instrument.

3. A securing apparatus as defined in claim 1, wherein the support face is dimensioned to vertically align the ablation element against the targeted tissue.

4. A securing apparatus as defined in claim 1, wherein the hermetic seal and said vacuum source cooperate to form a vacuum force sufficient to retain said ablation device against said biological tissue.

5. A securing apparatus as defined in claim 1, wherein the support face is deformable to substantially conform to the shape of the biological tissue.

6. A securing apparatus as defined in claim 1, wherein the support face forms suction cup.

7. A securing apparatus as defined in claim 1, wherein the support base is disposed proximate a distal end of the ablating element.

8. A securing apparatus as defined in claim 1, wherein the support base is disposed proximate a proximal end of the ablating element.

9. A securing apparatus as defined in claim 1, wherein said orifice includes a plurality of orifices spaced apart peripherally about said window portion.

10. A securing apparatus as defined in claim 1, wherein said proximal and distal orifices are about 1 mm to about 2 mm in diameter.

11. A securing apparatus for selectively securing an ablating element of an ablation instrument proximate to a targeted region of a biological tissue comprising:

a support base adapted to couple to the ablation instrument, and defining a window portion configured to cooperate with the ablating element to direct a majority of an ablating field of the ablating element generally in a predetermined direction, said support base further defining a passage terminating at a support face of the support base at a proximal orifice positioned on a proximal end of said window portion, and at a distal orifice positioned on a distal end of said window portion;

a vacuum line in fluid communication with the passage; and a vacuum source operatively coupled to the vacuum line, and formed to generate a vacuum force sufficient to hermetically seal the support member against the biological tissue to secure the ablation instrument thereto.

12. A securing apparatus as defined in claim 11, wherein the support face is dimensioned to vertically align the ablation element against the targeted tissue.

13. A securing apparatus as defined in claim 11, wherein the support face is deformable to substantially conform to the shape of the biological tissue.

14. A securing apparatus as defined in claim 11, wherein said orifice includes a plurality of orifices spaced apart peripherally about said window portion.

15. A securing apparatus as defined in claim 11, wherein said proximal and distal orifices are about 1 mm to about 2 mm in diameter.

16. A microwave ablation instrument for ablating biological tissue, comprising:

a transmission line having a proximal portion suitable for connection to an electromagnetic energy source;

an antenna coupled to the transmission line for generating an electric field sufficiently strong to cause tissue ablation; and a shield assembly coupled to the antenna to substantially shield a surrounding area of the antenna from the electric field radially generated therefrom while permitting a majority of the field to be directed generally in a predetermined direction, said shield assembly including:

a support base having a support face adapted to seat against the biological tissue proximate to the antenna, and defining a passage having one end coupled to a vacuum source and an opposite end terminating at an orifice at the support face; wherein said support face forms a hermetic seal against the biological tissue during operation of said vacuum source to secure the ablation instrument thereto.

17. A microwave ablation instrument as defined in claim 16, wherein the transmission line is suitable for transmission of microwave energy at frequencies in the range of approximately 800 to 6000 megahertz.

18. A microwave ablation instrument as defined in claim 16, wherein the antenna generates an electric field sufficiently strong to cause tissue ablation in a radial direction.

19. A securing apparatus as defined in claim 16, wherein the support face is dimensioned to vertically align the ablation element against the targeted tissue.

20. A securing apparatus as defined in claim 16, wherein the support face is deformable to substantially conform to the shape of the biological tissue.

21. A securing apparatus as defined in claim 16, wherein said support face defines a window portion cooperating with the ablating element to direct a majority of an ablating field of the ablating element generally in a predetermined direction.

22. A securing apparatus as defined in claim 21, wherein said orifice includes a proximal orifice positioned on a proximal end of said window portion, and a distal orifice positioned on a distal end of said window portion.

23. A securing apparatus as defined in claim 22, wherein said orifice includes a plurality of orifices spaced apart peripherally about said window portion.

24. A securing apparatus as defined in claim 21, wherein said proximal and distal orifices are about 1 mm to about 2 mm in diameter.

* * * * *